United States Patent
Wang et al.

(10) Patent No.: US 11,918,987 B2
(45) Date of Patent: Mar. 5, 2024

(54) PREPARATION METHOD FOR PROPYLENE EPOXIDATION CATALYST AND USE THEREOF

(71) Applicant: Wanhua Chemical Group Co., Ltd., Yantai (CN)

(72) Inventors: Lei Wang, Yantai (CN); Tongji Wang, Yantai (CN); Fei Ye, Yantai (CN); Kang Sun, Yantai (CN); Naibo Chu, Yantai (CN); Qiankun Jiao, Yantai (CN); Yuan Li, Yantai (CN)

(73) Assignee: Wanhua Chemical Group Co., Ltd., Yantai (CN)

( * ) Notice: Subject to any disclaimer, the term of this patent is extended or adjusted under 35 U.S.C. 154(b) by 536 days.

(21) Appl. No.: 17/291,250

(22) PCT Filed: Jan. 14, 2020

(86) PCT No.: PCT/CN2020/072098
§ 371 (c)(1),
(2) Date: May 4, 2021

(87) PCT Pub. No.: WO2021/142635
PCT Pub. Date: Jul. 22, 2021

(65) Prior Publication Data
US 2022/0305479 A1  Sep. 29, 2022

(51) Int. Cl.
| | |
|---|---|
| *B01J 37/00* | (2006.01) |
| *B01J 21/06* | (2006.01) |
| *B01J 21/08* | (2006.01) |
| *B01J 23/28* | (2006.01) |
| *B01J 35/10* | (2006.01) |
| *B01J 37/08* | (2006.01) |
| *C07D 301/14* | (2006.01) |

(52) U.S. Cl.
CPC ......... *B01J 37/0018* (2013.01); *B01J 21/063* (2013.01); *B01J 21/08* (2013.01); *B01J 23/28* (2013.01); *B01J 35/1023* (2013.01); *B01J 35/1061* (2013.01); *B01J 37/08* (2013.01); *C07D 301/14* (2013.01); *B01J 2523/31* (2013.01); *B01J 2523/41* (2013.01); *B01J 2523/47* (2013.01); *B01J 2523/68* (2013.01)

(58) Field of Classification Search
CPC ...... B01J 37/0015; B01J 21/063; B01J 21/08; B01J 23/28; B01J 35/1023; B01J 35/1061; B01J 37/08; B01J 2523/31; B01J 2523/41; B01J 2523/47; B01J 2523/68; C07D 301/14
USPC ......... 502/107, 242, 255, 309; 549/523–525, 549/529
See application file for complete search history.

(56) References Cited

U.S. PATENT DOCUMENTS

| | | | | |
|---|---|---|---|---|
| 4,021,454 A | * | 5/1977 | Wulff | C07D 303/02 549/529 |
| 4,891,437 A | * | 1/1990 | Marquis | C07D 303/04 549/529 |
| 5,081,267 A | | 1/1992 | Rameswaran et al. | |
| 5,723,637 A | * | 3/1998 | Tsuji | C07D 301/19 549/529 |
| 6,096,910 A | * | 8/2000 | Yamamoto | B01J 35/108 549/529 |
| 7,273,941 B2 | * | 9/2007 | Strickler | C07C 29/132 549/523 |
| 11,291,985 B2 | * | 4/2022 | Wang | B01J 21/08 |
| 2003/0097009 A1 | * | 5/2003 | Oku | C07D 301/19 549/529 |
| 2018/0147560 A1 | * | 5/2018 | Hsu | B01J 37/04 |

FOREIGN PATENT DOCUMENTS

| | | | |
|---|---|---|---|
| BE | 773363 | 3/1972 | |
| CN | 1051356 | 5/1991 | |
| CN | 102755910 | 10/2012 | |
| CN | 106964337 | 7/2017 | |
| CN | 107715868 A | 2/2018 | |
| CN | 110773147 A * | 2/2020 | ............. B01J 23/28 |
| CN | 110947375 A * | 4/2020 | ............. B01J 23/002 |
| CN | 112898237 A * | 6/2021 | ............. B01J 21/08 |
| JP | 2018087121 A | 6/2018 | |

OTHER PUBLICATIONS

English translation of Written Opinion for PCT/CN2020/072098. (Year: 2020).*
Office Action dated Aug. 14, 2023 by the Saudi Authority for IP in the corresponding Patent Application No. 521422382, with English translation.
International Search Report issued in Corresponding PCT Application No. PCT/CN2020/072098, dated Sep. 29, 2020 (English Translation provided).
Office Action dated Jan. 5, 2022 by the CIPO in the corresponding Patent Application No. 202010038571.X, with English translation.
Office Action dated Apr. 19, 2022 by the JPO in the corresponding Patent Application No. 2021-519775, with English translation.

* cited by examiner

*Primary Examiner* — Patricia L. Hailey
(74) *Attorney, Agent, or Firm* — Norton Rose Fulbright US LLP; James R. Crawford

(57) ABSTRACT

Provided are a preparation method for a propylene epoxidation catalyst, and a use thereof. During the preparation, an alkoxide solution of a prepared active component and a silica gel support are mixed, then a rotary evaporation treatment is performed on the mixture to remove a low-carbon alcohol to obtain a catalyst precursor, and then the obtained catalyst precursor is subjected to calcination and silylation treatments to obtain the propylene epoxidation catalyst. The catalyst is prepared in a simple process, can be applied to the chemical process of preparing propylene oxide by propylene epoxidation, has high average selectivity to propylene oxide, and has industrial application prospect.

15 Claims, No Drawings

PREPARATION METHOD FOR PROPYLENE EPOXIDATION CATALYST AND USE THEREOF

CROSS REFERENCE TO RELATED APPLICATIONS

The present application is a national phase application under 35 U.S.C. § 371 of International Application No. PCT/CN2020/072098, filed Jan. 14, 2020, the entire contents of which are incorporated herein by reference in their entirety.

TECHNICAL FIELD

The present disclosure relates to a preparation method for a propylene epoxidation catalyst, a catalyst prepared, and a use of the catalyst for catalyzing an epoxidation reaction of propylene to propylene oxide.

BACKGROUND

The ethylbenzene co-oxidation process (PO/SM) using ethylbenzene hydroperoxide (EBHP) as an oxidizing agent and the combined heat and power (CHP) process using cumene hydroperoxide (CHP) as an oxidizing agent are two important processes for producing propylene oxide. These two processes overcome the disadvantages of the chlorohydrination process, such as large corrosion and sewage, and have the advantages of low production cost and small environmental contamination.

The catalyst used in the epoxidation step of the heterogeneous PO/SM process is a Ti—$SiO_2$ composite oxide. U.S. Pat. No. 3,829,392 and US2003166951, and Chinese Published Patent Nos. CN1894030A and CN1720100A disclose the preparation method of this catalyst, including the following steps: drying a silica gel support, then carrying titanium halide vapor into a reaction tube to chemically react with silica gel with $N_2$ or other inert gas (this step is referred to as chemical vapor deposition), calcining at a high temperature, washing with water to remove Cl, and finally silylating to obtain the catalyst. The catalyst used in the CHP process is also the Ti—$SiO_2$ composite oxide. U.S. Pat. Nos. 6,211,388 and 5,744,619 disclose a sol-gel process for preparing this catalyst, including the following steps: dissolving a silicon source and a titanium source separately in an alcohol solvent, adding a quaternary ammonium ion (such as cetylammonium bromide) as a template, performing hydrolysis, polymerization, and aging to form a gel, and then performing calcination at a high temperature, crushing and molding, and silylation to obtain the catalyst. The titanium active species of the catalyst prepared by the chemical vapor deposition method has poor dispersibility on the $SiO_2$ surface and easily forms free $TiO_2$, resulting in ineffective decomposition of the oxidizing agent and reduction of PO selectivity. Compared with the vapor deposition method, the sol-gel method can make different components miscible with each other at the molecular level to obtain the nano-phase region or even the molecularly dispersed titanium active center. One of the greatest drawbacks of the sol-gel process, however, is that expensive quaternary ammonium salts need to be added as a template in the preparation process and that the template generally needs to be removed by high-temperature calcination, so that the template cannot be recovered, resulting in high catalyst costs. At the same time, these two methods have common disadvantages, that is, the preparation steps are lengthy, the requirements for the preparation conditions are high, and the production cost is high.

In addition, in order to improve the performance of the catalyst, CN106964337A discloses a Ti—Mo—$SiO_2$ epoxidation catalyst, in which Ti and Mo are supported on a silica gel support in two steps, and after the Mo is supported on the silica gel support, a solvent for dissolving the Mo source needs to be washed off with an organic solvent. Since the silica gel support has a large specific surface area and a small pore size, it is difficult to wash off all of the solvent when cleaning the solvent of the Mo source, thereby affecting the performance of the catalyst. At the same time, separation is required when the solvent is reused, and the steps are cumbersome and the economy is poor.

On the basis of the drawbacks of existing epoxidation catalysts, a new catalyst preparation method that is highly selective for PO and has a simple production step needs to be developed.

SUMMARY

The object of the present disclosure is to provide a preparation method for a propylene epoxidation catalyst. The method has a simple preparation process, and the catalyst prepared has great activity and is highly selective to PO.

To achieve the object of the present disclosure, the present disclosure adopts the following technical solution:

a preparation method for a propylene epoxidation catalyst, including the following steps:
  (1) titanate and ammonium molybdate are dissolved in a low-carbon alcohol, and mixed with a silica gel support to perform a rotary evaporation treatment to remove the low-carbon alcohol to obtain a catalyst precursor;
  (2) a calcination treatment is performed on the catalyst precursor obtained in step (1) at elevated temperature to obtain an oxide catalyst; and
  (3) a silylation treatment is performed on the oxide catalyst obtained in step (2) using a silylating reagent to obtain the propylene epoxidation catalyst.

In step (1) of the present disclosure, the titanate and the ammonium molybdate are dissolved in the low-carbon alcohol to obtain an alcohol solution containing titanium and molybdenum, where the titanate may be one or more selected from the group consisting of tetramethyl titanate, tetraethyl titanate, tetrapropyl titanate, tetraisopropyl titanate, tetrabutyl titanate, and tetraisobutyl titanate. In one embodiment, the amount of Ti in the titanate is 2% to 5% of the mass of silica gel in step (1), for example, 2.2%, 3%, 4% or 4.8%. The concentration of the titanate in the low-carbon alcohol is 1% to 10%, for example, 1.1% to 9.9%, preferably, 2% to 8%, for example, 3%, 5%, or 7%.

In step (1) of the present disclosure, the low-carbon alcohol may be those well known in the art that can be conveniently removed by rotary evaporation, for example, C1-C4, such as methanol, ethanol, isopropanol, and the like. The water content of the low-carbon alcohol should be as low as possible under more preferred conditions, for example, a low-carbon alcohol with the water content of lower than 10 ppm or anhydrous alcohol.

In step (1) of the present disclosure, ammonium molybdate having good compatibility with titanate and silica gel is selected as a molybdenum source and dissolved in the low-carbon alcohol. In one embodiment, the molar ratio of Mo to Ti in the obtained alcohol solution may be 0.05:1 to 0.2:1, for example, 0.06:1, 0.1:1, 0.15:1, or 0.18:1. It has been found that the addition of a certain amount of ammonium molybdate as a molybdenum source has a good effect on the modification of the catalyst (Mo exists in the form of the oxide $MoO_3$ in the catalyst, and some Mo, like Ti, enters into the skeleton of $SiO_2$), so that it is beneficial for a better synergistic effect with Ti to improve the selectivity of the catalyst to PO and the conversion of the peroxide, and the usage amount of molybdenum is low.

In step (1) of the present disclosure, the silica gel is used as a precursor of amorphous silica in the catalyst so that a good impregnation effect can be achieved in the rotary evaporation process of the alcohol solution and the dispersion effect of Mo and Ti on the silica gel support is good. The silica gel support (that is, silica gel) used in the present disclosure is well known in the art. In one embodiment, the silica gel support in step (1) has an equivalent spherical diameter of 0.5 to 3 mm, for example, 1 mm or 2 mm, and has a specific surface area of 500 m²/g or more, for example, 800 to 900 m²/g. Such silica gels have developed voids to facilitate the dispersion of the active species, for example, it has an average pore size of 2 to 10 nm, for example, 2 to 3 nm. In addition, the metal elements such as sodium and iron in the silica gel should be as low as possible, for example, by weighting in the form of an oxide, the NaO content is less than 50 ppm, and the iron oxide content is less than 50 ppm.

The rotary evaporation process used in step (1) of the present disclosure is well known in the art. For example, a rotary evaporation treatment carried out by a rotary evaporator or other rotary evaporation apparatus may be performed at a rotational speed of 10 to 100 rpm, or the rotary evaporation treatment may be performed under vacuum. For example, the pressure may be controlled to be 100 to 50 Kpa and the temperature may be 50° C. to 70° C. to remove the low-carbon alcohol solvent. As the low-carbon alcohol solvent evaporates, the active components are gradually dispersed on the surface of the silica gel, and the dispersion effect on the surface of the silica gel is good. The evaporated low-carbon alcohol can be condensed and recycled, further reducing costs.

In step (2) of the present disclosure, the catalyst precursor obtained in step (1) is calcined at elevated temperature to decompose the titanate, ammonium molybdate and silica gel therein. According to the preparation method of the present disclosure, preferably, the catalyst precursor is calcined at elevated temperature under an ammonia atmosphere. It has been found that the calcination at elevated temperature under the ammonia atmosphere not only reamers the catalyst precursor to form more pore structures, so that more active species such as Ti are exposed to improve the catalytic activity, but also surprisingly, enables N to enter the $SiO_2$ skeleton after calcination so that the synergistic effect with Mo and Ti improves the selectivity of the catalyst to PO. In one embodiment, the content of N (that is, N entering the $SiO_2$ skeleton) in the resulting oxide catalyst after calcination is greater than 0.2 wt %, for example, 0.25 wt %, 0.29 wt %, 0.47 wt %, or 0.5 wt %.

In one embodiment, the calcination at elevated temperature in step (2) is a two-stage programmed calcination at elevated temperature under an ammonia atmosphere. The temperature is first elevated to 140° C. to 160° C., for example, 148° C. to 155° C. or 150° C., at a $NH_3$ space velocity of 2 to 5 h$^{-1}$, for example, 2.5 h$^{-1}$, 3 h$^{-1}$, or 4h$^{-1}$, and the calcination is performed for 1 to 3 h, for example, 2 h (i.e. the first-stage calcination); then the temperature is elevated to 450° C. to 600° C., for example, 500° C. or 550° C., at a $NH_3$ space velocity of 0.4 to 2 h$^{-1}$, for example, 0.5 h$^{-1}$, 1.25 h$^{-1}$, or 1.5 h$^{-1}$, and the calcination is performed for 2 to 5 h, for example, 3 h or 4 h (i.e. the second-stage calcination). The temperature elevation rate is not particularly required. For example, the temperature may be elevated at a temperature elevation rate of 1° C./min to 3° C./min. The "$NH_3$ space velocity" refers to the value of ammonia flow per unit time divided by the mass of the silica gel support.

In the above-mentioned process, the first-stage calcination is firstly carried out to facilitate the reaming of the catalyst precursor. The purpose of reaming is to make the catalyst form a certain pore structure, so that more active Ti species are exposed and the reactants are brought into contact with the active center. The average pore size of the catalyst obtained after reaming may be up to 7.9 to 12 nm. In addition, the first-stage calcination is also beneficial to avoid that water in the solution when aqueous ammonia or ammonium saline or alkali metal solution is used for reaming causes the already-formed skeleton Ti species to become free $TiO_2$ which in turn reduces the selectivity of the catalyst to PO. The subsequent second-stage calcination facilitates the entry of Ti and Mo into the $SiO_2$ skeleton of the support to form the active center and immobilize the active components, and meanwhile, more advantageously, enables N to enter the $SiO_2$ skeleton under the ammonia atmosphere so that the synergistic effect of N with Mo and Ti improves the selectivity of the catalyst to PO.

In step (3) of the present disclosure, the residual hydroxyl in the product of step (2) is silylated using the silylating reagent to improve the surface hydrophobicity of the catalyst. The silylating reagent may be a silylating reagent commonly used in the art, for example, the silylating reagent may be hexamethyldisilazane, trimethylsilyl diethylamine, or trimethylsilyl alkylimidazole, and the amount of the silylating reagent is 5 to 15 wt % of the mass of the silica gel support, for example, 8 wt % or 12 wt %. The specific silylation treatment may be performed by carrying steam of the silylating reagent (such as hexamethyldisilazane) into a reaction tube by $N_2$ with a silylation temperature of 200° C. to 300° C. and a silylation duration of 120 to 180 min. The chemical reaction occurring during the silylation treatment is as follows:

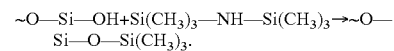

$\sim$O—Si—OH+Si(CH$_3$)$_3$—NH—Si(CH$_3$)$_3$→$\sim$O—Si—O—Si(CH$_3$)$_3$.

The above silylation treatment can improve the surface hydrophobicity of the catalyst, reduce the ability of the catalyst to decompose the peroxide, and improve the selectivity of the catalyst to PO.

The present disclosure also provides the use of the propylene epoxidation catalyst prepared by the above preparation method in catalyzing the propylene epoxidation reaction. For example, the propylene epoxidation reaction is a reaction in which propylene is reacted with cumene hydroperoxide as an oxidizing agent to prepare propylene oxide. Preferably, in the reaction, the molar ratio of propylene to cumene hydroperoxide is 5:1 to 7:1 and the weight hourly space velocity is 2 to 3.5 hr$^{-1}$. At the start of the reaction, the temperature may be low, for example, 50° C. to 60° C., and the reaction temperature may be gradually increased according to the CHP conversion (ensuring that the CHP conversion is greater than 99%).

The present disclosure has the following technical effects:

(1) in the present disclosure, the preparation step is simple, a template does not need to be used, the process conditions are not severe, and the conditions are easy to control, so that the industrialization is easy to realize;

(2) the solvent in the present invention, that is, the low-carbon alcohol, is easily recycled so that the waste liquid is reduced and the cost is reduced; and (3) when the catalyst precursor in the present disclosure is calcined under the ammonia atmosphere, the catalyst can be reamed or modified, and N can enter the $SiO_2$ skeleton so that the synergistic action of N with Mo and Ti improves the selectivity of the catalyst to PO.

DETAILED DESCRIPTION

For a better understanding of the present disclosure, the content of the present disclosure will be further illustrated below in conjunction with examples, but is not limited to the examples set forth below.

In the present disclosure, unless otherwise specified, the percentages used are all percentages by mass.

The specific surface area and pore structure in the examples of the present disclosure were determined by the BET method ($N_2$ physical adsorption method) with the instrument No. ASP2020 manufactured by Micromeritics Instrument Corporation, USA.

The content of N in the catalyst in the examples of the present disclosure was determined by using an oxygen/nitrogen/hydrogen determinator No. ONH836 manufactured by LECO Corporation, USA.

The content of PO in the reaction liquid and tail gas absorption liquid was analyzed by gas chromatography in the examples of the present disclosure, and the conversion rate of CHP was analyzed by iodometry. The chromatographic analysis conditions are shown in Table 1.

TABLE 1

| Operating conditions for chromatography | |
|---|---|
| Chromatographic column | Agilent 19091N-133 (30 m*250 μm*0.25 μm) |
| $H_2$ flow rate | 35 mL/min |
| Air flow rate | 350 mL/min |
| Tail-blowing flow rate ($N_2$) | 25 mL/min |
| Heater | 270° C. |
| Column oven | 250° C. |
| Temperature programming | Initial temperature 50° C. Temperature programmed 50° C. to 100° C. 15° C./min maintain for 0 min 100° C. to 250° C. 20° C./min maintain for 2 min |
| Injection port split ratio | 30:1 |
| FID detector temperature | 270° C. |

The content of PO was determined by internal standard method. The liquid concentration was determined using DMF as the solvent and dioxane (DT) as the internal standard, and the standard curve of internal standard of PO and DT was determined to be y=0.6985x−0.0046, R2=0.999. The concentration of PO in the gas-phase absorption liquid was determined using toluene as the internal standard, and the standard curve of internal standard of PO and toluene was determined to be y=2.161x+0.0002, R2=0.999.

Liquid PO concentration=(0.6985×($A_{PO}/A_{DT}$)−0.0046)× 0.01×dilution scale

Liquid PO content=liquid PO concentration×liquid sampling mass

Gas PO concentration=(2.162×($A_{PO}/A_{toluene}$)+0.0002)× toluene mass

Gas PO content=gas PO concentration×total absorption liquid/gas-phase sampling mass Total PO production=gas PO content+liquid PO content PO selectivity=Total PO production/theoretical amount of PO produced by propylene capable of being oxidized by CHP×100%

The CHP conversion was titrated by iodometry and determined using a titrator.

CHP conversion=(CHP initial value−CHP remaining amount)/CHP initial value

CHP remaining amount=(titration end-point−blank)× $CNa_2S_2O_3$×0.001×0.5×142×total liquid sampling amount/titration sampling amount The titanate used in the examples was tetrabutyl titanate, and the low-carbon alcohol was anhydrous ethanol.

The silica gel support used in the examples of the present disclosure was manufactured by Bokai Silica Gel Co., Ltd. The silica gel support had an equivalent spherical diameter of 1.2 mm, a specific surface area of 852 $m^2/g$, an average pore size of 2.6 nm, a Na content of about 30 ppm, and an iron content of 27 ppm.

The catalyst in the Examples and Comparative Examples was used for preparing propylene oxide by propylene epoxidation under the following conditions: the oxidizing agent was cumene hydroperoxide (CHP), the reaction tube was a fixed bed reactor with an inner diameter of 24 mm, the loading volume of the catalyst was 20 g, the molar ratio of propylene to CHP was 7:1, the weight hourly space velocity was 3.5 $hr^{-1}$, and the reaction temperature was gradually increased according to the CHP conversion (ensuring that the CHP conversion is greater than 99%) with the initial reaction temperature of 50° C.

EXAMPLE 1

7.08 g of tetrabutyl titanate and 0.21 g of ammonium molybdate were dissolved in 200 g of ethanol which was denoted as solution a. Then 40 g of silica gel and the solution a were mixed and added to a rotary evaporation flask. The flask was heated and rotated by rotary evaporation at a heating temperature of 50° C. and a rotation speed of 30 rpm, and then vacuumized by a vacuum pump at a pressure of 50 KPa. The rotary evaporation impregnation was performed until the silica gel surface was dried to obtain a catalyst precursor. The catalyst precursor was added to a tubular furnace, and the temperature elevation rate was set to 2° C./min. The catalyst precursor was calcined at 150° C. for 3 h at a flow rate of $NH_3$ of 100 g/h, and then calcined at an elevated temperature of 450° C. for 3 h at a flow rate of $NH_3$ of 20 g/h. The sample obtained after calcination was subjected to gas-phase silylation treatment: 6 g of hexamethyldisilazane was added to a vaporization tank and heated at a heating temperature of 130° C., and the steam of hexamethyldisilazane was carried into a reaction tube by $N_2$ and reacted with the sample obtained after calcination, in which the linear velocity of $N_2$ in the reaction tube was 1 cm/s, the silylation temperature was 200° C., and the silylation duration was 180 min. The resulting catalyst was denoted as TM-01.

The average pore size of the TM-01 catalyst was determined by the BET method to be 8.9 nm. The content of N in the catalyst was determined by an oxygen/nitrogen/hydrogen determinator to be 0.29%. TM-01 was evaluated by continuous operation for 680 hr with the reaction temperature elevated from initially 50° C. to 60° C. The sample was analyzed by gas chromatography. The CHP conversion was greater than 99.9%, and the selectivity to PO was up to 97.9%, with an average of 96.9%.

EXAMPLE 2

9.92 g of tetrabutyl titanate and 0.57 g of ammonium molybdate were dissolved in 200 g of ethanol which was denoted as solution a. Then 40 g of silica gel and the solution a were mixed and added to a rotary evaporation flask. The flask was heated and rotated by rotary evaporation at a heating temperature of 50° C. and a rotation speed of 50 rpm, and then vacuumized by a vacuum pump at a pressure of 60 KPa. The rotary evaporation impregnation was performed until the silica gel surface was dried to obtain a catalyst precursor. The catalyst precursor was added to a tubular furnace, and the temperature elevation rate was set to 2° C./min. The catalyst precursor was calcined at 150° C. for 3 h at a flow rate of $NH_3$ of 150 g/h, and then calcined at an elevated temperature of 550° C. for 4 h at a flow rate of $NH_3$ of 40 g/h. The sample obtained after calcination was subjected to gas-phase silylation treatment: 4 g of hexamethyldisilazane was added to a vaporization tank and heated at a heating temperature of 140° C., and the steam of hexamethyldisilazane was carried into a reaction tube by $N_2$ and reacted with the sample obtained after calcination, in which the linear velocity of $N_2$ in the reaction tube was 0.5 cm/s, the silylation temperature was 250° C., and the silylation duration was 120 min. The resulting catalyst was denoted as TM-02.

The average pore size of the TM-02 catalyst was determined by the BET method to be 10.1 nm. The content of N in the catalyst was determined by an oxygen/nitrogen/hydrogen determinator to be 0.39%. TM-02 was evaluated by continuous operation for 1200 hr with the reaction temperature elevated from initially 50° C. to 70° C. The sample was analyzed by gas chromatography. The CHP conversion was greater than 99.9%, and the selectivity to PO was up to 98.2%, with an average of 98%.

EXAMPLE 3

11.33 g of tetrabutyl titanate and 0.98 g of ammonium molybdate were dissolved in 200 g of ethanol which was denoted as solution a. Then 40 g of silica gel and the solution a were mixed and added to a rotary evaporation flask. The flask was heated and rotated by rotary evaporation at a heating temperature of 60° C. and a rotation speed of 70 rpm, and then vacuumized by a vacuum pump at a pressure of 80 KPa. The rotary evaporation impregnation was performed until the silica gel surface was dried to obtain a catalyst precursor. The catalyst precursor was added to a tubular furnace, and the temperature elevation rate was set to 2° C./min. The catalyst precursor was calcined at 150° C. for 2 h at a flow rate of $NH_3$ of 180 g/h, and then calcined at an elevated temperature of 600° C. for 2 h at a flow rate of $NH_3$ of 50 g/h. The sample obtained after calcination was subjected to gas-phase silylation treatment: 3.2 g of hexamethyldisilazane was added to a vaporization tank and heated at a heating temperature of 150° C., and the steam of hexamethyldisilazane was carried into a reaction tube by $N_2$ and reacted with the sample obtained after calcination, in which the linear velocity of $N_2$ in the reaction tube was 0.6 cm/s, the silylation duration was 100 min, and the silylation temperature was 300° C. The resulting catalyst was denoted as TM-03.

The average pore size of the TM-03 catalyst was determined by the BET method to be 11.1 nm. The content of N in the catalyst was determined by an oxygen/nitrogen/hydrogen determinator to be 0.44%. TM-03 was evaluated by continuous operation for 980 hr with the reaction temperature elevated from initially 50° C. to 90° C. The sample was analyzed by gas chromatography. The CHP conversion was greater than 99.9%, and the selectivity to PO was up to 97.9%, with an average of 96.5%.

EXAMPLE 4

14.16 g of tetrabutyl titanate and 1.63 g of ammonium molybdate were dissolved in 200 g of ethanol which was denoted as solution a. Then 40 g of silica gel and the solution a were mixed and added to a rotary evaporation flask. The flask was heated and rotated by rotary evaporation at a heating temperature of 70° C. and a rotation speed of 100 rpm, and then vacuumized by a vacuum pump at a pressure of 100 KPa. The rotary evaporation impregnation was performed until the silica gel surface was dried to obtain a catalyst precursor. The catalyst precursor was added to a tubular furnace, and the temperature elevation rate was set to 2° C./min. The catalyst precursor was calcined at 150° C. for 2 h at a flow rate of $NH_3$ of 200 g/h, and then calcined at an elevated temperature of 550° C. for 5 h at a flow rate of $NH_3$ of 80 g/h. The sample obtained after calcination was subjected to gas-phase silylation treatment: 2.6 g of hexamethyldisilazane was added to a vaporization tank and heated at a heating temperature of 140° C., and the steam of hexamethyldisilazane was carried into a reaction tube by $N_2$ and reacted with the sample obtained after calcination, in which the linear velocity of $N_2$ in the reaction tube was 0.5 cm/s, the silylation temperature was 250° C., and the silylation duration was 120 min. The resulting catalyst was denoted as TM-04.

The average pore size of the TM-04 catalyst was determined by the BET method to be 11.8 nm. The content of N in the catalyst was determined by an oxygen/nitrogen/hydrogen determinator to be 0.47%. TM-04 was evaluated by continuous operation for 600 hr with the reaction temperature elevated from initially 60° C. to 75° C. The sample was analyzed by gas chromatography. The CHP conversion was greater than 99.9%, and the selectivity to PO was up to 97.8%, with an average of 97.1%.

COMPARATIVE EXAMPLE 1

The difference of Comparative example 1 from Example 2 lied in that the calcination was performed under a nitrogen atmosphere and the resulting catalyst was denoted as TS-21.

The average pore size of the TS-21 catalyst was determined by the BET method to be 2.5 nm. TS-21 was evaluated by continuous operation for 200 hr with the reaction temperature elevated from initially 50° C. to 80° C. The sample was analyzed by gas chromatography. The CHP conversion was greater than 99.9%, and the selectivity to PO was up to 13.9%, with an average of 11%.

COMPARATIVE EXAMPLE 2

9.92 g of tetrabutyl titanate and 0.57 g of ammonium molybdate were dissolved in 200 g of ethanol which was denoted as solution a. Then 40 g of silica gel and the solution a were mixed and added to a rotary evaporation flask. The flask was heated and rotated by rotary evaporation at a heating temperature of 50° C. and a rotation speed of 50 rpm, and then vacuumized by a vacuum pump at a pressure of 60 KPa. The rotary evaporation impregnation was performed until the silica gel surface was dried to obtain a catalyst precursor. The catalyst precursor was added to a tubular furnace, and the temperature elevation rate was set to 2° C./min. The catalyst precursor was calcined at 150° C. for 3 h at a flow rate of $NH_3$ of 150 g/h, and then calcined at an elevated temperature of 550° C. for 4 h at a flow rate of $N_2$ of 40 L/h. The sample obtained after calcination was subjected to gas-phase silylation treatment: 4 g of hexamethyldisilazane was added to a vaporization tank and heated at a heating temperature of 140° C., and the steam of hexamethyldisilazane was carried into a reaction tube by $N_2$ and reacted with the sample obtained after calcination, in which the linear velocity of $N_2$ in the reaction tube was 0.5 cm/s, the silylation temperature was 250° C., and the silylation duration was 120 min. The resulting catalyst was denoted as TM-22.

The average pore size of the TM-22 catalyst was determined by the BET method to be 10.1 nm. No N was detected in the catalyst by an oxygen/nitrogen/hydrogen determinator. TM-22 was evaluated by continuous operation for 200 hr with the reaction temperature elevated from initially 50° C. to 70° C. The sample was analyzed by gas chromatography. The CHP conversion was greater than 99.8%, and the selectivity to PO was up to 95.9%, with an average of 94.4%.

What is claimed is:

1. A preparation method of a propylene epoxidation catalyst, comprising the following steps:
   (1) titanate and ammonium molybdate are dissolved in a low-carbon alcohol, and mixed with a silica gel support to perform a rotary evaporation treatment to remove the low-carbon alcohol to obtain a catalyst precursor;
   (2) a calcination treatment is performed on the catalyst precursor obtained in step (1) at elevated temperature to obtain an oxide catalyst; and
   (3) a silylation treatment is performed on the oxide catalyst obtained in step (2) using a silylating reagent to obtain the propylene epoxidation catalyst.

2. The preparation method according to claim 1, wherein in step (2), the catalyst precursor is calcined at elevated temperature under an ammonia atmosphere.

3. The preparation method according to claim 2, wherein in step (2), calcination process conditions are: a calcination atmosphere is ammonia gas, and a two-stage temperature programming is adopted, in which in a first stage, a calcination temperature is 140° C. to 160° C., a calcination duration is 1 to 3 h, and a space velocity of the ammonia gas is 2 to 5 $h^{-1}$, and in a second stage, a calcination temperature is 450° C. to 600° C., a calcination duration is 3 to 5 h, and a space velocity of the ammonia gas is 0.4 to $2^{-1}$.

4. The preparation method according to claim 2, wherein in step (2), the content of N in the oxide catalyst obtained after the calcination treatment is greater than 0.2 wt %.

5. The preparation method according to claim 1, wherein in step (1), the amount of Ti in the titanate is 2 to 5 wt % of the mass of the silica gel support in step (1), and the concentration of the titanate in the low-carbon alcohol is 1 to 10 wt %.

6. The preparation method according to claim 5, wherein in step (1), the amount ratio of titanate to ammonium molybdate is such that the molar ratio of Mo to Ti is 0.05:1 to 0.2:1.

7. The preparation method according to claim 1, wherein the titanate in step (1) is one or more selected from the group consisting of tetramethyl titanate, tetraethyl titanate, tetrapropyl titanate, tetraisopropyl titanate, tetrabutyl titanate, and tetraisobutyl titanate.

8. The preparation method according to claim 1, wherein the silica gel support in step (1) has an equivalent spherical diameter of 0.5 to 3 mm and a specific surface area of 800 to 900 $m^2/g$.

9. The preparation method according to claim 8, wherein during the rotary evaporation treatment in step (1), a rotary evaporation speed is 10 to 100 rpm, a rotary evaporation temperature is 50° C. to 70° C., and a pressure is 50 to 100 KPa.

10. The preparation method according to claim 1, wherein the silica gel support in step (1) has an average pore size of 2 to 3 nm.

11. The preparation method according to claim 1, wherein the silylating reagent in step (3) is hexamethyldisilazane, and the temperature of the silylation treatment is 200° C. to 300° C.

12. The preparation method according to claim 1, wherein the amount of the silylating reagent in step (3) is 5 to 15 wt % of the mass of the silica gel support, and the duration of the silylation treatment is 60 to 180 min.

13. A preparation method of propylene oxide, wherein the method uses the propylene epoxidation catalyst prepared by the preparation method according to claim 1 in catalyzing a propylene epoxidation reaction.

14. The preparation method according to claim 13, wherein the propylene epoxidation reaction is a reaction in which propylene is reacted with cumene hydroperoxide as an oxidizing agent to prepare propylene oxide.

15. The preparation method according to claim 14, wherein the molar ratio of the propylene to the cumene hydroperoxide is 5:1 to 7:1, and a weight hourly space velocity is 2 to 3.5 $h^{-1}$.

* * * * *